US010524601B2

(12) United States Patent
Bing et al.

(10) Patent No.: US 10,524,601 B2
(45) Date of Patent: Jan. 7, 2020

(54) ARTICLE AND METHOD FOR CONTROLLING ODORS FROM ODORIFEROUS NITROGEN-CONTAINING COMPOUNDS

(71) Applicant: Cintas Corporation, Cincinnati, OH (US)

(72) Inventors: Richard R. Bing, West Chester, OH (US); Patrick J. Chilenski, Cincinnati, OH (US); Jeffery L. Cofer, Conyers, GA (US); Sylvester Holston, III, Cincinatti, OH (US); Ian S. Malpass, Palm Beach Gardens, FL (US); David Mesko, Wyoming, OH (US)

(73) Assignee: Cintas Corporate Services, Inc., Cincinnati, OH (US)

( * ) Notice: Subject to any disclaimer, the term of this patent is extended or adjusted under 35 U.S.C. 154(b) by 242 days.

(21) Appl. No.: 15/197,848

(22) Filed: Jun. 30, 2016

(65) Prior Publication Data

US 2017/0007057 A1 Jan. 12, 2017

Related U.S. Application Data

(60) Provisional application No. 62/190,300, filed on Jul. 9, 2015.

(51) Int. Cl.
*A61L 9/012* (2006.01)
*A47G 27/02* (2006.01)

(52) U.S. Cl.
CPC .......... *A47G 27/0206* (2013.01); *A61L 9/012* (2013.01); *A47G 2400/02* (2013.01)

(58) Field of Classification Search
CPC .. A47G 27/0206; A47G 2400/02; A61L 9/012
See application file for complete search history.

(56) References Cited

U.S. PATENT DOCUMENTS 4,285,075 A 8/1981 Nelson
6,099,771 A * 8/2000 Hudkins ................. B29C 43/56 264/102
6,159,576 A * 12/2000 Rockwell, Jr. .......... A47L 23/26 428/95
6,974,691 B2 * 12/2005 Fredenburgh ............. A61L 9/01 435/252.1
7,314,748 B1 1/2008 Fredenburgh et al.
D604,799 S 11/2009 Sand et al.
8,726,945 B2 5/2014 Sand et al.
2003/0126688 A1 * 7/2003 Peters ................. D06M 16/003 8/115.51
2003/0135938 A1 * 7/2003 Tyler ...................... B41M 5/035 8/467
2005/0119447 A1 * 6/2005 Boyle .................. C08K 5/3412 528/310

FOREIGN PATENT DOCUMENTS

CN 104924709 A * 9/2015

OTHER PUBLICATIONS

Lemieux et al., Destruction of Spores on Building Decontamination Residue in a commericial Autoclave, Dec. 2006, Applied and Enviromental Microbiology, vol. 72 No. 12, pp. 7687-7693.*

* cited by examiner

*Primary Examiner* — Ali Soroush

(74) *Attorney, Agent, or Firm* — Wood Herron & Evans LLP

(57) ABSTRACT

An article includes a surface adapted for presence in an environment containing odoriferous nitrogen-containing compounds, a bonding agent, and bacilli bacteria. A method for binding bacilli to a surface is also disclosed. First, the surface is provided. The surface is then heated and placed under pressure. Then, the bacilli and a bonding agent may be applied to the surface, either alone or as a pre-mixed composition. The pre-mixed composition may be in the form of an aqueous dispersion. A method for controlling odors from odoriferous nitrogen-containing compounds is also disclosed. The method includes applying bacilli bacteria to a surface and placing the surface in an area likely to include odoriferous nitrogen-containing compounds.

18 Claims, 1 Drawing Sheet

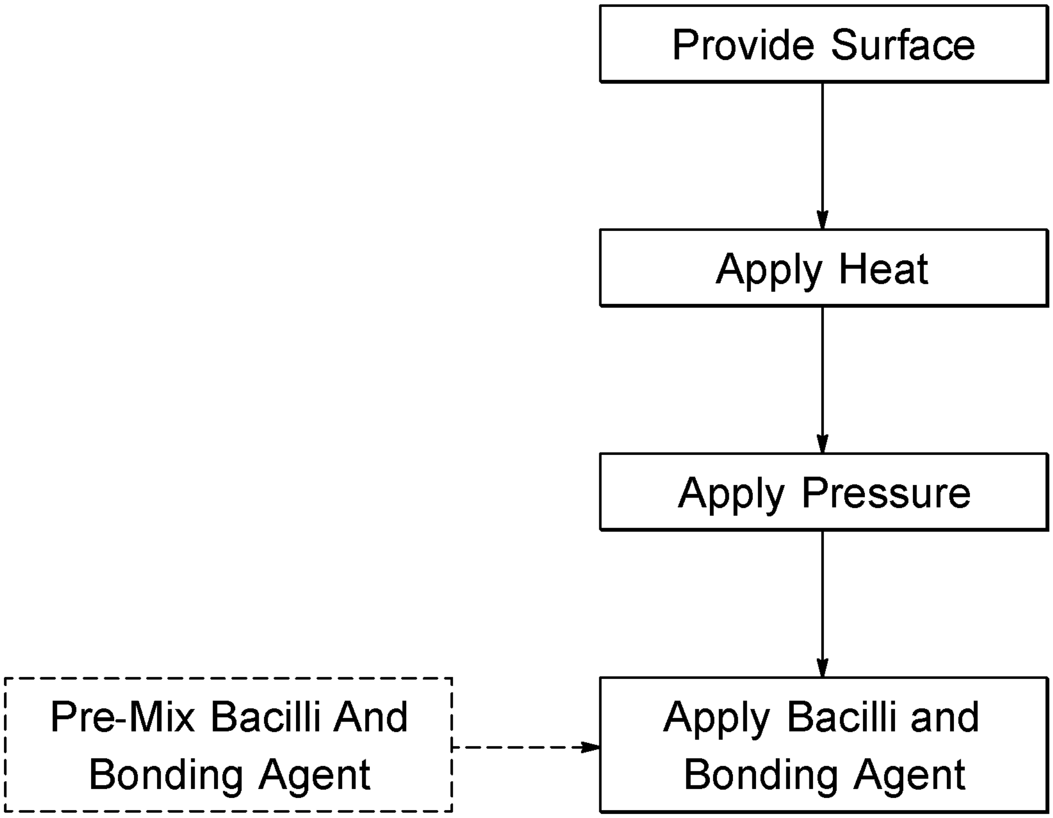
Provide Surface
Apply Heat
Apply Pressure
Pre-Mix Bacilli And Bonding Agent
Apply Bacilli and Bonding Agent

ARTICLE AND METHOD FOR CONTROLLING ODORS FROM ODORIFEROUS NITROGEN-CONTAINING COMPOUNDS

CROSS-REFERENCE TO RELATED APPLICATION

This application is related and claims priority to U.S. Provisional Patent Application Ser. No. 62/190,300, filed on Jul. 9, 2015, the entire contents of which are herein incorporated by reference.

FIELD

The present invention is generally related to the field of odor control, and more particularly, to articles and methods for controlling odors from odoriferous nitrogen-containing compounds.

BACKGROUND

Restroom mats help to prevent slip-and-fall type accidents in restrooms. The mats may be used to absorb bodily fluids that have inadvertently been left behind after use of the restroom, as well as provide a non-slip surface on which to walk and stand.

A common contaminant in restrooms is urine. Urine, which comprises greater than 95% water, is a solution of urea, chloride, sodium, potassium, creatinine, other dissolved ions, and other inorganic and organic compounds. The nitrogen-containing compounds in urine, or those that are products of further degradation of urea, may exhibit quite a pungent odor. The odor tends to strengthen over time if not treated promptly. In a public restroom, especially, this issue may be difficult to control because of high use of the restroom and insufficient resources available for cleaning the restrooms promptly.

Most known urine treatment products are applied retroactively. Thus, once contamination of a surface by urine has taken place, that surface must be cleaned to prevent or minimize the pungent odors associated with that contamination. Additionally, these post-treatment regimens must be performed after each contamination event.

SUMMARY

In an attempt to overcome the noted deficiencies, the present invention is directed toward articles and methods for controlling odors from odoriferous nitrogen-containing compounds.

The present invention is premised on the realization that bacilli bacteria may digest odoriferous nitrogen-containing compounds when present on surfaces residing in areas containing such nitrogen-containing compounds. In a first embodiment of the present invention, an article is provided that includes a surface adapted for presence in an environment containing odoriferous nitrogen-containing compounds, a bonding agent, and bacilli bacteria.

In another embodiment of the invention, a method is provided for binding bacilli to a surface. First, the surface is provided. The surface is then heated and placed under pressure. Then, the bacilli and a bonding agent may be applied to the surface, either alone or as a pre-mixed composition. The pre-mixed composition may be in the form of an aqueous dispersion.

In yet another embodiment of the invention, a method is provided for controlling odors from odoriferous nitrogen-containing compounds. The method includes applying bacilli bacteria to a surface and placing the surface in an area likely to include odoriferous nitrogen-containing compounds.

A further embodiment of the invention is an article for controlling odors from odoriferous nitrogen-containing compounds. The article may be a restroom or floor mat which includes bacilli bacteria on a surface of the mat in an area likely to include the odoriferous nitrogen-containing compounds.

The objects and advantages of the present invention will be further appreciated in light of the following detailed description and drawings provided herein.

BRIEF DESCRIPTION OF THE DRAWINGS

The accompanying drawings, which are incorporated in and constitute a part of this specification, illustrate embodiments of the invention and, together with a general description of the invention given above and the detailed description given below, serve to explain the principles of the invention.

FIG. 1 is a schematic of a method to produce an embodiment of the inventive article.

DETAILED DESCRIPTION

Unless clearly defined otherwise from the context, any range of values presented in the following Detailed Description and Claims includes each end point as well as each whole number or fractional part thereof, within the recited range. Additionally, approximating language may be applied to modify any quantitative representation that may vary without resulting in a change in the basic function to which it is related. Accordingly, a value modified by a term or terms, such as "about" and "substantially," may not be limited to the precise value specified.

If appearing herein, the term "comprising," or derivatives thereof, is not intended to exclude the presence of any additional component, step, or procedure, whether or not the same is disclosed herein. In order to avoid any doubt, all compositions claimed herein through use of the term "comprising" may include any additional additive, adjuvant, or compound, unless stated to the contrary. The terms "comprising" and "including" (or derivatives thereof) are intended to be synonyms. In contrast, the term, "consisting essentially of" if appearing herein, excludes from the scope of any succeeding recitation any other component, step, or procedure, excepting those that are not essential to operability. The term "consisting of," if used, excludes any component, step, or procedure not specifically delineated or listed. The term "or," unless stated otherwise, refers to the listed members individually as well as in any combination.

According to exemplary embodiments of the present invention, an article is provided that includes a surface present in an environment containing odoriferous nitrogen-containing compounds, a bonding agent, and bacilli bacteria. The surface may include carpets, mats, rugs, or any other surface expected to be contaminated with odoriferous nitrogen-containing compounds. One example of an article according to this invention is a mat for use on the floor of a bathroom, such as the mat disclosed in U.S. Pat. No. 4,285,075, which patent is incorporated by reference in its entirety herein.

Odoriferous nitrogen-containing compounds include urea and its metabolic products, including ammonia. Areas expected to contain odoriferous nitrogen-containing compounds include animal shelters, kennels, restrooms, and certain chemical manufacturing plants. Odoriferous nitrogen-containing compounds are especially troublesome in public restrooms, because depending on the volume of use, immediate cleaning after a surface is contaminated with such compounds may not be possible.

The bonding agent, sometimes also referred to as an "adhering agent," may be any agent known to assist the binding of bacilli to the material of the surface. Exemplary bonding agents are disclosed in U.S. Pat. No. 7,314,748, entitled "Odor Control Agent," the contents of which are incorporated herein by reference.

The bacilli may be Generally Recognized as Safe and may be capable of fixing nitrogen. One source of bacilli for the presently disclosed invention is BACILOX®, a mixture of *bacillus* strains, produced by OSPREY BIOTECHNICS, Inc. of Sarasota, Fla.

In another embodiment of the present invention, a method is provided for binding bacilli to a surface. First, the surface is provided. The surface may then be heated and placed under pressure. Then, the bacilli and a bonding agent may be applied to the surface, either alone or as a pre-mixed composition. The pre-mixed composition may be in the form of an aqueous dispersion.

As discussed above, the surface may be a carpet, a mat, a rug, or any other surface expected to be contaminated with odoriferous nitrogen-containing compounds. Surfaces containing fibrous weaves are well-suited for this invention.

The surface may then be heated and placed under pressure, either simultaneously or in sequence. Heating may take place in an oven or press at 250° F. to 450° F. The temperature of the oven may be any whole integer ranging 250° F. to 450° F., inclusive of the endpoints, or fractional part thereof, such as 350° F. to 450° F. or 390° F. to 440° F. or 410° F. to 430° F. For instance, the surface may be placed in an oven at about 420° F.

In one embodiment, the heating and placing under pressure occur in sequence. After the time provided for heating discussed above, the oven may be cooled and then pressure may be applied. The applied pressure may range from 100 psi to 400 psi or from 150 psi to 350 psi or from 200 psi to 300 psi or about 300 psi or any fractional portion thereof. This pressure may be applied for 1 s to 20 s or for 5 s to 15 s or for about 10 s or for any fractional amount of time thereof.

The direct application of heating and/or pressure may take place for a time ranging from about 1 second to about 10 seconds or more. For instance, the direct application of heating and/or pressure may take place for about 5 seconds. In certain embodiments, a heat press may be used, and the heat press may undergo a cycle time. For instance, the heat press may cycle by warming over about 10 seconds, applying the heating and/or pressure described above for about 1 second to about 10 seconds, and then cooling for an additional about 10 seconds. Thus, in certain embodiments, the entire heating and/or application of pressure may take place over about 20 seconds to about 30 seconds. These times may be varied, and one of ordinary skill in the art is capable of selecting an appropriate amount of time for each particular application.

The bacilli and the bonding agent are then applied to the surface. In practice, commercially-available bacilli strains may be pre-mixed with the bonding agent, or a dispersion of the bacilli may be applied separately from a solution of the bonding agent.

The combined bacilli and bonding agent may be dispersed in water at concentrations by weight of 1%, 2%, 3%, 4%, 5%, 6%, 7%, 8%, 9%, 10%, 11%, 12%, 13%, 14%, 15%, 16%, 17%, 18%, 19%, 20%, or any fractional part thereof.

Any convenient method of application can be performed. For example, the surface may be soaked in a vat of the dispersion and/or solution. Alternatively, a mixture of the bacilli and bonding agent in water can be sprayed onto the surface. The bacilli may be applied to the surface at a concentration ranging from 1 g/$m^2$ to 10 g/$m^2$. For instance, the concentration may be 1 g/$m^2$, 2 g/$m^2$, 3 g/$m^2$, 4 g/$m^2$, 5 g/$m^2$, 6 g/$m^2$, 7 g/$m^2$, 8 g/$m^2$, 9 g/$m^2$, 10 g/$m^2$, or any fractional part thereof.

This process is depicted schematically in FIG. 1.

In another embodiment of the invention, a method is provided for controlling odors from odoriferous nitrogen-containing compounds. The method includes applying bacilli bacteria to a surface and placing the surface in an area likely to include odoriferous nitrogen-containing compounds. The bacilli bacteria are applied as described above. After the surface is treated with the bacilli, the bacteria lay dormant until the bacilli are contacted with the odoriferous nitrogen-containing compounds. Urease in the bacilli then consumes the odoriferous nitrogen-containing compounds in a manner known to those of ordinary skill in the art. The inventors have found that the bacteria may lay dormant for up to 5 years.

The present invention will be further appreciated in view of the following example.

Example

A needlepunch polyester mat with a duragon backing is cut into 71 inch long by 48 inch wide sections. These sheets are placed into a compression press inside a two part compression mold machined to have a cavity that forms the finished shape of the urinal mat. There are six urinal mat cavities per mold. The 48 inch by 71 inch sheet covers all six molding areas. The press is heated to 425° F. The press is then closed and pressure is applied at about 300 psi for 10 s. After this time, the press is opened and the formed surface is immediately sprayed with a 5:1 by weight water to bacilli/bonding agent mixture. In total 108 g of the mixture is sprayed over the surface. The six treated mats are stacked and another sheet is placed in the press. These mats may then be punched to size on a punch press and steel die combination. Alternatively, the cutting can take place on the press if a specially adapted press is used.

This has been a description of the present invention along with the various methods of practicing the present invention. However, the invention itself should only be defined by the appended claims.

What is claimed is:

1. A method for binding bacilli to a surface of an article, said method comprising: providing the article including the surface;

next, heating the surface of the article at a temperature and placing the surface of the article under a pressure for a period of time between 1 s and 20 s, wherein the pressure is in the range from 200 psi to 400 psi; and applying the bacilli and a bonding agent to the surface that was heated and placed under pressure; wherein the bacilli and the bonding agent are applied to the surface separately or as a premixed composition.

2. The method of claim 1, wherein the heating takes place in an oven or press at 250° F. to 450° F.

3. The method of claim 2, wherein the heating takes place in an oven or press at 450° F.

4. The method of claim 1, wherein the pressure is about 300 psi.

5. The method of claim 1, wherein the pressure is applied for about 10 s.

6. The method of claim 1, wherein the article is a floor mat.

7. The method of claim 1, wherein placing the surface of the article under the pressure takes place in a compression press.

8. The method of claim 7, wherein the compression press includes a cavity, and placing the surface of the article under the pressure comprises shaping the article to have a finished shape based on the cavity.

9. The method of claim 1, wherein the heating and placing the surface under the pressure occur in sequence.

10. The method of claim 9, further comprising, after heating the surface at the temperature and before placing the surface under the pressure, cooling the surface.

11. A method for binding bacilli to a surface of an article, said method comprising: providing the article including the surface;

next, heating the surface of the article at a temperature and placing the surface of the article under a pressure for a period of time between 1 s and 20 s, wherein the pressure is in the range from 100 psi to 400 psi; wherein the heating and placing the surface under the pressure occur in sequence; after heating the surface at the temperature and before placing the surface under the pressure, cooling the surface; and applying the bacilli and a bonding agent to the surface that was heated and placed under pressure; wherein the bacilli and the bonding agent are applied to the surface separately or as a premixed composition.

12. The method of claim 11, wherein the heating takes place in an oven or press at 250° F. to 450° F.

13. The method of claim 12, wherein the heating takes place in an oven or press at 450° F.

14. The method of claim 11, wherein the pressure is about 300 psi.

15. The method of claim 11, wherein the pressure is applied for about 10 s.

16. The method of claim 11, wherein the article is a floor mat.

17. The method of claim 11, wherein placing the surface of the article under the pressure takes place in a compression press.

18. The method of claim 17, wherein the compression press includes a cavity, and placing the surface of the article under the pressure comprises shaping the article to have a finished shape based on the cavity.

* * * * *